US011235322B2

(12) United States Patent
Dysli et al.

(10) Patent No.: US 11,235,322 B2
(45) Date of Patent: Feb. 1, 2022

(54) ANALYTICAL SYSTEM WITH ACCURATE POSITIONING OF MULTIWELL PLATES

(71) Applicant: Roche Molecular Systems, Inc., Pleasanton, CA (US)

(72) Inventors: Lukas Dysli, Aarau (CH); Christian Thalmann, Kehrsiten (CH)

(73) Assignee: Roche Molecular Systems, Inc., Pleasanton, CA (US)

(*) Notice: Subject to any disclaimer, the term of this patent is extended or adjusted under 35 U.S.C. 154(b) by 593 days.

(21) Appl. No.: 15/718,634

(22) Filed: Sep. 28, 2017

(65) Prior Publication Data
US 2018/0147574 A1    May 31, 2018

(30) Foreign Application Priority Data

Sep. 30, 2016   (EP) .................................... 16191771

(51) Int. Cl.
*B01L 3/00*    (2006.01)
*B01L 9/00*    (2006.01)
(Continued)

(52) U.S. Cl.
CPC ......... *B01L 3/502715* (2013.01); *B01L 9/523* (2013.01); *C12Q 1/686* (2013.01);
(Continued)

(58) Field of Classification Search
CPC .. B01L 3/5025; B01L 3/5085; B01L 3/50853; B01L 3/50855; B01L 3/23; B01L 3/0829; B01L 3/0893; B01L 2300/0829; B01L 2300/0893; B01L 9/523; G01N 35/028
See application file for complete search history.

(56) References Cited

U.S. PATENT DOCUMENTS 5,110,556 A * 5/1992 Lyman ................ B01L 3/50255
                                                356/246
5,456,360 A   10/1995 Griffin
(Continued)

FOREIGN PATENT DOCUMENTS

CN      1549921 A   11/2004
CN    102127596 A    7/2011
(Continued)

OTHER PUBLICATIONS

EP16191771.1 Search Report.

*Primary Examiner* — Jill A Warden
*Assistant Examiner* — Dwayne K Handy
(74) *Attorney, Agent, or Firm* — Maneesh Gupta

(57) ABSTRACT

The present disclosure relates to an analytical system with at least three components: a multiwell plate on which the wells are included in an optically transparent area; a frame holding the multiwell plate close to its edge while permitting the plate a certain extent of freedom of movement; a baseplate to which the multiwell plate, but not the frame is firmly fixed via a docking mechanism, such that different expansion of plate and frame can be compensated. A second aspect described herein relates to a method of docking a corresponding multiwell plate held by a frame to a baseplate and subjecting the multiwell plate to a step of a biological or chemical assay within this arrangement.

11 Claims, 9 Drawing Sheets

(51) Int. Cl.
*G01N 35/02* (2006.01)
*C12Q 1/686* (2018.01)
*G01N 35/04* (2006.01)

(52) U.S. Cl.
CPC ...... *G01N 35/028* (2013.01); *B01L 2200/025* (2013.01); *B01L 2200/026* (2013.01); *B01L 2200/028* (2013.01); *B01L 2300/0609* (2013.01); *B01L 2300/0627* (2013.01); *B01L 2300/0829* (2013.01); *B01L 2300/0858* (2013.01); *B01L 2300/0877* (2013.01); *B01L 2300/0893* (2013.01); *G01N 2035/042* (2013.01)

(56) References Cited

U.S. PATENT DOCUMENTS

| | | | |
|---|---|---|---|
| 6,171,780 B1 * | 1/2001 | Pham | B01L 3/5085 422/552 |
| 6,485,690 B1 * | 11/2002 | Pfost | B01J 19/0046 422/552 |
| 2005/0205673 A1 | 9/2005 | Morris et al. | |
| 2011/0306097 A1 | 12/2011 | Belz et al. | |
| 2014/0274739 A1 | 9/2014 | Rinker et al. | |

FOREIGN PATENT DOCUMENTS

| | | |
|---|---|---|
| EP | 2338597 A1 | 6/2011 |
| EP | 2607904 | 6/2013 |

* cited by examiner

ANALYTICAL SYSTEM WITH ACCURATE POSITIONING OF MULTIWELL PLATES

CROSS-REFERENCE TO RELATED APPLICATIONS

The present application claims the benefit of priority under 35 U.S.C. § 119(a) of 16191771.1, filed Sep. 30, 2016. Reference is also made to EP16183569.9, filed Aug. 10, 2016; EP16002058.2 and EP16002057.4, each filed Sep. 23, 2016; EP16191425.4, filed Sep. 29, 2016; and EP16191811.5, EP16400044.0, each filed September 30. The disclosures of each of these applications are incorporated herein by reference in their entireties.

FIELD OF THE DISCLOSURE

The present disclosure belongs to the field of analytical systems for conducting biological or chemical assays. Within this field, it relates to the positioning of multiwell plates within such systems in order to ensure accuracy in certain steps of biological or chemical assays.

BACKGROUND

For the purpose of analyzing multiple biological samples, well plates, or more particularly multiwell plates, have been widely used as standard tools in analytical research and clinical diagnostic testing laboratories, often in the form of a consumable for one-time use. The standardization of the formats of multiwell plates, most notably according to ANSI/SLAS (formerly SBS), in particular in view of the arrangement of its wells, provides a significant advantage since the standardization allows the use of standardized laboratory devices such as robotic handling devices, automated sample handling devices, sample dispensers, as well as multiwell plate readers or reaction observation devices. With special regard to readers or observation devices, optical detection is the most commonly used method for measuring reactions, particularly with regard to arrays of wells representing a multitude of different reactions.

Biological or chemical assays that are usually carried out in such multiwell plates often require incubation at various different temperatures. For instance, Polymerase Chain Reaction (PCR) relies on multiple rounds of applying extreme temperature changes during a relatively short period of time. Such conditions impose considerable mechanical stress on the involved components such as the reaction vessels that may be provided in the form of a multiwell plate.

Oftentimes, such reaction vessels are held in a frame made of a material different from the material of the reaction vessels. The usage of frames allows for improved handling of the vessels, mechanical protection, supporting a plurality of single reaction vessels, and the like.

The frame on one hand and the reaction vessels/multiwell plates on the other hand mostly need to fulfill different requirements due to the nature of their respective tasks. In many cases, the vessels have to be made of a transparent material in order to permit the passage of a light beam for optical detection measures. Moreover, at least the inner walls of the vessels should generally be chemically inert such that they do not interfere with the biological or chemical reactions taking place on the inside. In other cases, the inside of the vessels is coated with specific reagents, reactants, capture molecules, or the like. As for the frame, the focus rests more on material properties such as robustness, flexibility, and the like, such that the frame provides protection and good handling properties.

As a consequence, frame and reaction vessels/multiwell plate are often made of different materials that exhibit corresponding different expansion properties, such as under changing influences as in thermal incubation processes or the like. The mechanical stress upon heating/cooling cycles such as in a PCR, causing differential thermal expansion in frame and multiwell plate, can lead to phenomena like warping, cracking, distortion, and the like, all potentially jeopardizing the integrity of the analytical system and thus the proper processing of the biological or chemical sample to be analyzed, including negative impact on handling, positioning, focusing during optical detection, and the like. These problems may even arise when multiwell plate and frame are made of the same material, since they may not be evenly subjected to mechanical/thermal stress and thus exhibit different extents of aging during their periods of usage. As an example, frame and multiwell plate may not be thermally coupled, so in a setup where only the multiwell plate is in contact with a heater, it may extend to a considerably larger extent than the frame. Another phenomenon potentially leading to differential expansion may be environmental humidity to which multiwell plate and frame may be differentially susceptible.

Approaches in the art to deal with this problem include U.S. Pat. No. 5,456,360A, where multiple individual reaction tubes are loosely held in the bore holes of a tube rack, whereas they become tightly immobilized along with the rack as soon as they are introduced into corresponding recesses in a baseplate.

However, the usage of multiwell plates instead of individual tubes for thermocycling, but also other analytical methods or method steps, poses additional challenges which are addressed by virtue of the measures described herein.

SUMMARY

In a first aspect described herein, an analytical system with at least three components is provided:
- a multiwell plate on which the wells are included in an optically transparent area
- a frame holding the multiwell plate close to its edge while permitting the multiwell plate a certain extent of freedom of movement
- a baseplate to which the multiwell plate, but not the frame is firmly fixed via a docking mechanism, such that different expansion of multiwell plate and frame can be compensated.

A second aspect described herein relates to a method of docking a corresponding multiwell plate held by a frame to a baseplate and subjecting the multiwell plate to a step of a biological or chemical assay within this arrangement.

BRIEF DESCRIPTION OF THE FIGURES

FIG. 1A shows frame and multiwell plate separately from above, FIG. 1B from below, and FIG. 1C shows perspective views from above and below of the frame holding the multiwell plates.

FIG. 4B shows a perspective view of the assembly, and finally FIG. 4C shows a cross-sectional side view of the optical path through the analytical system within the optical detection system.

DETAILED DESCRIPTION

Figure 1A:
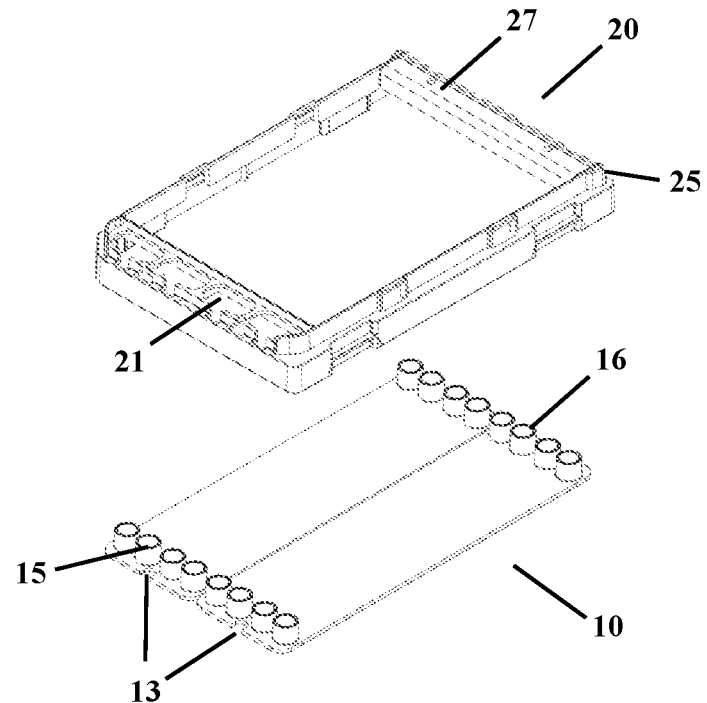
FIGS. 1A-1C provide perspective views of the multiwell plate and the frame of the analytical system described herein.

A first aspect described herein is an analytical system for conducting a biological or chemical assay, the system comprising the following components:

a multiwell plate comprising a plurality of wells in an optically transparent area, the multiwell plate having a first docking structure spaced apart from the optically transparent area;

a frame holding the multiwell plate at its rim with sufficient lateral clearance to spatially compensate for differential expansion of frame and multiwell plate;

a baseplate having a second docking structure corresponding to the first docking structure for firmly laterally positioning the multiwell plate with its plurality of wells in the optically transparent area relative to the baseplate;

wherein there is no direct fixture between the frame and the baseplate, such that the lateral clearance between frame and multiwell plate is maintained even when the frame is docked to the baseplate.

The analytical system described herein confers a number of advantages over the approaches used previously in the art.

For instance, the optically transparent area can be made accessible for a light beam passing through it within the analytical system. In other words, the specific arrangement of multiwell plate, frame, and baseplate provide the possibility of positioning the wells of the multiwell plate within the optical path of a detection system, as immobilization is achieved by fixing the multiwell plate outside of the area to be optically analyzed. Thus, while the technical setup disclosed in U.S. Pat. No. 5,456,360A is focused on engaging individual sample tubes to a thermocycler for the direct transmission of thermal energy, the analytical system described herein exhibits the flexibility to be used not only in connection with a thermocycler or other thermal incubation device, but additionally with an optical detection system, a sample preparation module, a filling station, or other systems or modules of an analytical apparatus.

At the same time, it allows for the compensation of differential expansion of frame and multiwell plate, such as differential thermal expansion as occurring in PCR experiments or the like. This property is even more important when a component of the analytical system described herein, particularly the frame, have already undergone a certain extent of aging. For instance, it is known in the art that frames such as the one described herein may shrink during their period of usage, which may in some cases be around a year. In addition, manufacturing tolerances leading to lot-to-lot variances, for example, due to different molds in mass-productions, may be detrimental to the compatibility of frame and multiwell plate in cases where there is no lateral clearance. The flexible suspension of the multiwell plate within the frame, as described herein, reduces the negative impact of such differential expansion phenomena by providing a sufficient extent of lateral clearance.

This renders the analytical system described herein valuable for a wide range of applications from basic research to clinical diagnostics.

For instance, digital PCR (dPCR) is a highly favorable method for determining the absolute amount of a specific target nucleic acid in a sample such as a biochemical, clinical, forensic sample, or the like. In this context, dPCR has the capacity of improving the accuracy, but also the sensitivity of more classical PCR versions such as quantitative realtime PCR based on comparison to an internal or external standard nucleic acid.

There are different experimental setups for performing dPCR analysis. They all have in common that a sample to be analyzed is partitioned within many separate regions, each of which is subjected to an individual PCR. This usually requires a dilution step sometimes referred to as "terminal dilution" prior to partitioning, allowing for each partition to statistically contain either none or only one single individual target nucleic acid molecule. Hence, on the basis of assuming that the molecule population follows a Poisson distribution, the absolute number of target DNA molecules in the sample (before partitioning) can be determined with high accuracy. This approach abolishes the need of a reference nucleic acid serving as a quantitation standard, the latter only allowing for the determination of a relative amount of target nucleic acid molecules.

The basic principle of digital PCR has first been described by Pamela Sykes et al. in 1992 (BioTechniques, Vol. 13. No. 3).

One widely applied experimental setup relies on the formation of aqueous droplets in a lipophilic phase. These droplets constitute partitions of a terminally diluted sample and are subjected to thermal incubation cycles, most commonly in flow channels forming part of microfluidic devices.

While such arrangements require a pump system, different temperature zones, and other instrument components, it is also possible to perform dPCRs in stationary partitions such as reaction zones on a multiwell plate. In some cases, standard plates like, for example, 96-well plates have been used to carry out such reactions. However, in order to obtain statistically relevant data leading to reliable results—especially in sensitive fields like clinical diagnostics, where the nature or continuation of a therapy often depends on the corresponding diagnosis—it is mostly necessary to include a considerably higher number of partitions in a dPCR-based assay. In applications like rare mutation analysis, about 100000 or even more individual PCR results may be required for a sound estimate of the absolute copy number of the target nucleic acid in a given sample. As it is desirable to still comply with a standard such as an ANSI/SLAS format, such partitions may have to be downscaled to microscopically small wells with volumes in the nano- or even picoliter range. The task of individually detecting each of the about 100000 or more results accordingly requires demanding optical setups with little room for spatial deviation when it comes to positioning the multiwell plate in an optical path or the like. Also, it is usually impossible to individually adjust the position of a single well in an integral multiwell plate.

Even very slight distortions due to, for example, differential expansion of the involved materials, may thus lead to invalid results and hence to the loss of valuable and often hardly replaceable sample material.

The analytical system described herein is able to compensate for the consequences of such differential expansion while firmly and accurately positioning a multiwell plate in an optical path or in other arrangements.

In the context described herein, a "multiwell plate" constitutes an essentially flat plate comprising a multitude of reaction chambers in the form of wells or cavities which are used as test tubes for samples to be subjected to biological or chemical assays, wherein the multiwell plate can be made from any suitable kind of available material, such as glass, plastics, quartz, or silicon and typically provides 6, 24, 48, 96, 384, 1536 or even more sample wells which are often arranged in a 2:3 rectangular matrix. In cases where the multiwell plate complies with ANSI/SLAS (previously known as SBS) standards, they may be directly used in or with equally standardized devices and systems, such as multipipettors, magnetic plates, optical analyzers, and the like. The wells of a multiwell plate may be chemically inert on the inside, such that they do not interfere with the analytical reactions taking place within. In other embodiments, they may be coated with binding molecules such as biomolecules. Examples for biomolecules that may act, for instance, as capture molecules for binding either a target nucleic acid or other nucleic acids, include sequence-specific nucleic acid capture probes, such as DNA or LNA (Locked Nucleic Acid) probes. Another example would be streptavidin for interaction with a biotin tag at the target nucleic acid. Multiwell plates useful in the context described herein may have wells with diameters or wrench sizes—measured at the well opening which may, for example, be round, polygonal such as hexagonal, or the like—in the micro- to millimeter range, for example from 1 µm to 1 mm, or from 5 µm to 500 µm, or from 10 µm to 250 µm, or from 30 µm to 200 µm, or from 40 µm to 120 µm, or from 60 µm to 100 µm. In some embodiments, the wells have a diameter or wrench size of about 80 µm.

With regard to the volume of an individual well of multiwell plates as described herein, a well may have a volume in the pico- to nanoliter range, such as from 1 pl to 100 nl, or from 5 pl to 50 nl, or from 10 pl to 1 nl, or from 50 pl to 500 pl, or from 75 pl to 250 pl. In some embodiments, the volume of a well is about 100 pl.

The number of wells in the optically transparent area of a multiwell plate as described herein may, for instance, be from 1000 to 1000000 wells, or from 5000 to 500000 wells, or from 10000 to 250000 wells, or from 20000 to 100000 wells. In some embodiments, the number of wells of a multiwell plate may be about 50000.

In order to transfer sample liquid or other liquids such as reagents into and out of the multiwell plate, the latter may comprise an inlet port and/or an outlet port. The inlet and/or the outlet port may be shaped to receive a pipette tip for dispensing (inlet) and/or withdrawing (outlet) the respective liquid. Further, they may be made of a different material than the main body of the multiwell plate.

Multiwell plates as described herein comprise their wells in an optically transparent area. Suitable materials conferring high optical transparency and a low level of autofluorescence include, for instance, glass, plastics, quartz, silicon, or the like. In some embodiments, the material is a cyclic olefin polymer (COP) or copolymer (COC). Other suitable materials are known to the person skilled in the art. In some embodiments, the entire multiwell plate is made of the same optically transparent material. In other embodiments, a non-transparent area, for example, towards the edges of the multiwell plate, may be made of a different material such as a more robust material for handling and protection purposes or the like.

The latter properties are also provided by the frame as described herein. The frame may be made of a more robust type of plastic, serving the frame's main purposes of protecting the multiwell plate from damage or contamination, providing a handling interface such as a gripping ridge for transporting the multiwell plate automatically (robotic grippers or the like) or manually, or in some embodiments embracing more than one multiwell plate and thus creating a unit with an increased number of wells. Suitable materials include polypropylene (PP), polyoxymethylene (POM), polycarbonate (PC), acrylonitrile butadiene styrene (ABS), or even non-plastic materials.

In some embodiments, the dimensions of the frame are according to the ANSI/SLAS standards.

These standards have been published by the Society for Laboratory Automation and Screening (SLAS) and can be found under URL: http://www.slas.org/resources/information/industry-standards/. In particular, the outside dimension of the base footprint is standardized as about 127.76 mm in length and 85.48 mm in width. Compliance with this format ensures usability of the frame holding the multiwell plate in or with any correspondingly standardized laboratory equipment. In the context of these formats, the inventors have found that the lateral clearance provided between multiwell plate and frame are in some embodiments according to the tolerances as displayed below in Table 1:

TABLE 1

Overview of manufacturing tolerances and length influence due to aging and temperature. The multiwell plate is denoted here as chip.

| | | Nominal Size (mm) | Manufacturing Tolerances (mm) | Aging 3 Years (mm) | | Thermal Contraction/Expansion (mm) | | | |
|---|---|---|---|---|---|---|---|---|---|
| | | | | | | Min temp instrument (@° C.) (mm) | QC test temp (@° C.) (mm) | Min temp instrument (@° C.) (mm) | QC test temp (@° C.) (mm) |
| Frame | Footprint length (worst case) | 127.76 | −0.50  0.50 | −0.38 | 0.00 | −0.17 | 0.00 | 0.30 | 1.67 |
| | Footprint width (worst case) | 85.48 | −0.50  0.50 | −0.26 | 0.00 | −0.12 | 0.00 | 0.20 | 1.12 |
| Chip | Length (WC) | 123.76 | −0.32  0.32 | −0.15 | 0.00 | −0.07 | 0.00 | 0.12 | 0.63 |
| | Width (WC) | 35.5 | −0.13  0.13 | −0.04 | 0.00 | −0.02 | 0.00 | 0.03 | 0.19 |

The frame may further comprise one or more of the elements selected from the group of a handle, a stacking mechanism, a hardware coding element, and an identification tag. While a handle facilitates transportation and the like, a stacking mechanism may contribute to saving storage space, grouping multiwell plates of a specific experiment, or the like. Hardware coding elements such as rounded or flattened corners, edges, protrusions, indentations, or the like, facilitate the correct orientation especially in the case of symmetrical plates and frames, like in the ANSI/SLAS standard footprint. Correct orientation is especially important in cases where the multiwell plate interacts with an instrument module in a specific spatial constellation. Identification tags may be, for instance, one- or two-dimensional barcodes or RFID tags. In less complex cases, they may be human-readable letter, numbers, or the like.

The baseplate is configured and arranged to receive and hold the multiwell plate by means of docking. While the baseplate and the multiwell plate thus directly interact with each other, there is no such direct connection between frame and baseplate, allowing for maintenance of the beneficial lateral clearance between multiwell plate and frame.

The baseplate may be part of a module within an analyzer. For instance, in accordance with the above-described advantages of the analytical system in connection with optical detection, in some embodiments the baseplate is functionally coupled to or an integral part of an optical detection system comprising a light source and a detector.

In such embodiments, it may be advantageous that the baseplate is either optically transparent or includes an opening in the area where the optically transparent area of the multiwell plate comes to rest when the multiwell plate is docked to the baseplate. This permits the passage of a light beam in transmission-based detection and/or analyses.

In embodiments where detection relies on, for example, reflection or scattering of a light beam, the baseplate need not be optically transparent or comprise an opening.

The same accounts for embodiments in which the baseplate is part of a different module such as an amplification station. In such a setup, the baseplate may comprise heating and/or cooling such as Peltier elements. Such elements may be an integral part of the baseplate and may be in thermal contact with the multiwell plate such that the sample partitions within the multiwell plate may be subjected to a series of temperature cycles in a digital PCR experiment. Heating and/or cooling elements comprised by the baseplate may also be useful in a sample preparation or a filling station, as the processes taking place therein often require incubation at specific temperatures. Thus, in some embodiments of the analytical system described herein, the baseplate comprises heating and/or cooling elements.

Alternatively or additionally, the baseplate may comprise a magnet. For instance, the magnet may consist of a plurality of magnetic pins that may be inserted into corresponding recesses in the bottom of the multiwell plate, or the magnet may be flat and brought into contact with the bottom of the multiwell plate without the involvement of any protrusions or indentations on one side or the other. Magnets in the baseplate may, for instance, interact with magnetic or magnetically attractable particles within the wells. Such particles are often used for binding nucleic acids to their surface and subsequently isolating them from other, undesired components of the sample.

In view of the above-mentioned possible purposes of the baseplate, the latter may be made of different materials. In the case of the baseplate having heating and/or cooling elements, it may be made of a highly thermally conductive material such as a metal or an alloy. Where the baseplate forms part of an optical detection module, it may at least comprise similar material as the multiwell plate in embodiments where it includes an optically transparent area corresponding to the optically transparent area of the multiwell plate.

In a sample preparation module, metal or an alloy may again be the material of choice, especially, ferro-, ferri-, para- or superparamagnetic.

The "first docking structure" of the multiwell plate can be any means for attaching it to its counterpart, the "second docking structure", of the baseplate. These two docking structures constitute a functional pair configured and arranged to interact with each other. In some embodiments, the first and the second docking structures are detachable from each other without destroying or damaging one or the other.

Also in some embodiments, the first docking structure is located substantially in the center of the length and/or width of the edge of the multiwell plate, thus further reducing any potential imprecision with regard to positioning.

The inventors have found it particularly advantageous when the first docking structure comprises an indentation, such as a recess or hole, which may in some embodiments be located at the edge of the multiwell plate. More specifically, the first docking structure may be located substantially in the center of the length and/or width of the edge of the multiwell plate.

Also, some embodiments employ a protrusion as a second docking structure. Evidently, this works especially well with an indentation as a first docking structure. Such a protrusion may be a pin such as a cylindrical pin with a copped top, a conical pin, or another suitable geometrical shape.

Likewise, the first docking structure may comprise a protrusion and the second docking structure may comprise an indentation.

The corresponding docking mechanism between the first docking structure and the second docking structure may be a press-fit, a force-fit, a snap-fit, a joint, a hook, or any other suitable docking mechanism as known to the person skilled in the art.

In a specific embodiment, the first docking structure is a half-circle-shaped indentation in the center of the short edge of a rectangular multiwell plate, corresponding to a cylindrical pin with a copped top protruding upwards from the baseplate. The pin snugly fits into the indentation such that the multiwell plate becomes immobilized in relation to the baseplate.

This property contributes to the flexibility of the analytical system described herein, as the frame holding the multiwell plate may interact with different baseplates within a given analyzer. In other words, some embodiments feature different analytical systems as described herein within an analyzer, wherein frame and multiwell plate remain identical, while the baseplate is different depending on the module in which frame and multiwell plate are processed at a given point in time.

Another aspect described herein is a method for conducting a biological or chemical assay, the method comprising the following steps:

a. providing a multiwell plate comprising a plurality of wells in an optically transparent area, the multiwell plate having a first docking structure spaced apart from the optically transparent area, wherein the multiwell plate is held at its rim by a frame with sufficient lateral clearance to spatially compensate for differential expansion of frame and multiwell plate;

b. docking the multiwell plate to a baseplate having a second docking structure corresponding to the first docking structure and thereby firmly laterally positioning the multiwell plate with its plurality of wells in the optically transparent area relative to the baseplate, while not fixing the frame and the baseplate directly to each other, such that the lateral clearance between frame and multiwell plate is maintained;

c. subjecting the firmly positioned multiwell plate to one or more steps of a biological or chemical assay.

The frame may also serve as a first means of orientation when positioning the multiwell plate on the baseplate. In other words, the actual docking in step b. is in some embodiments preceded by a rough positioning of the multiwell plate via the frame. In these embodiments, the frame usually has a greater lock-in range than the multiwell plate itself, so that the frame may be advantageously used for pre-positioning.

Also in some embodiments, the one or more steps of a biological or chemical assay in step c. comprise one or more elements selected from the group consisting of optical detection, incubation at one or more different temperatures, pipetting, separation, and mixing, as described above in the context of the analytical system.

In another embodiment, step c. comprises thermal incubation in a thermal incubation system and optical detection in an optical detection system, which in a particular embodiment are performed sequentially—one after another—with a first baseplate being part of the thermal incubation system and a second baseplate being part of the optical detection system. In a specific embodiment, thermal incubation comprises steps a., b., and c. using the first baseplate, followed by the optical detection also comprising steps a., b., and c. using the second baseplate.

In these embodiments, the same setup can be advantageously used, such that the frame/multiwell plate assembly carrying the target analyte in its wells can be passed through thermocycling and subsequent detection while benefitting from the advantages described herein and using the same structures.

Furthermore, all embodiments or examples described in the context of the analytical system described herein, including its components, also apply to the method disclosed herein.

Examples

FIG. 1 shows perspective views of an embodiment of the multiwell plate (10) and the frame (20) as described herein and their interrelation or interaction, respectively.

The exploded view of FIG. 1A depicts the frame (20) from above prior to holding two identical multiwell plates (10) depicted underneath, also viewed from above. In this embodiment, the frame (20) comprises gaps (21) for inlet ports (15) present on each of the multiwell plates (10), while the corresponding outlet ports (16) are covered by a ridge (27) of the frame (20). It can be seen that each multiwell plate (10) includes four inlet ports (15) for entry of a liquid sample, thus contributing to an increased sample throughput as the frame (20) holds two individual multiwell plates (10) adding up to a total of eight inlet ports (15) through which a fluid sample is directed through a flow-through channel (17) by capillary forces until it reaches its corresponding outlet port (16). In some embodiments, pressure or a vacuum may be applied to the flow-through channels (17) via inlet ports (15) and/or outlet ports (16).

Figure 1B:
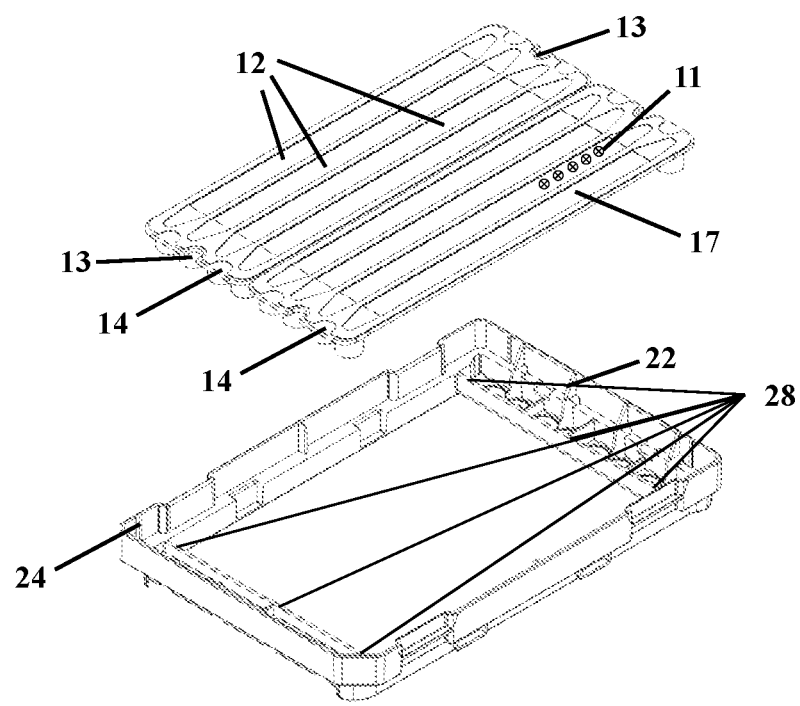
Figure 1C:
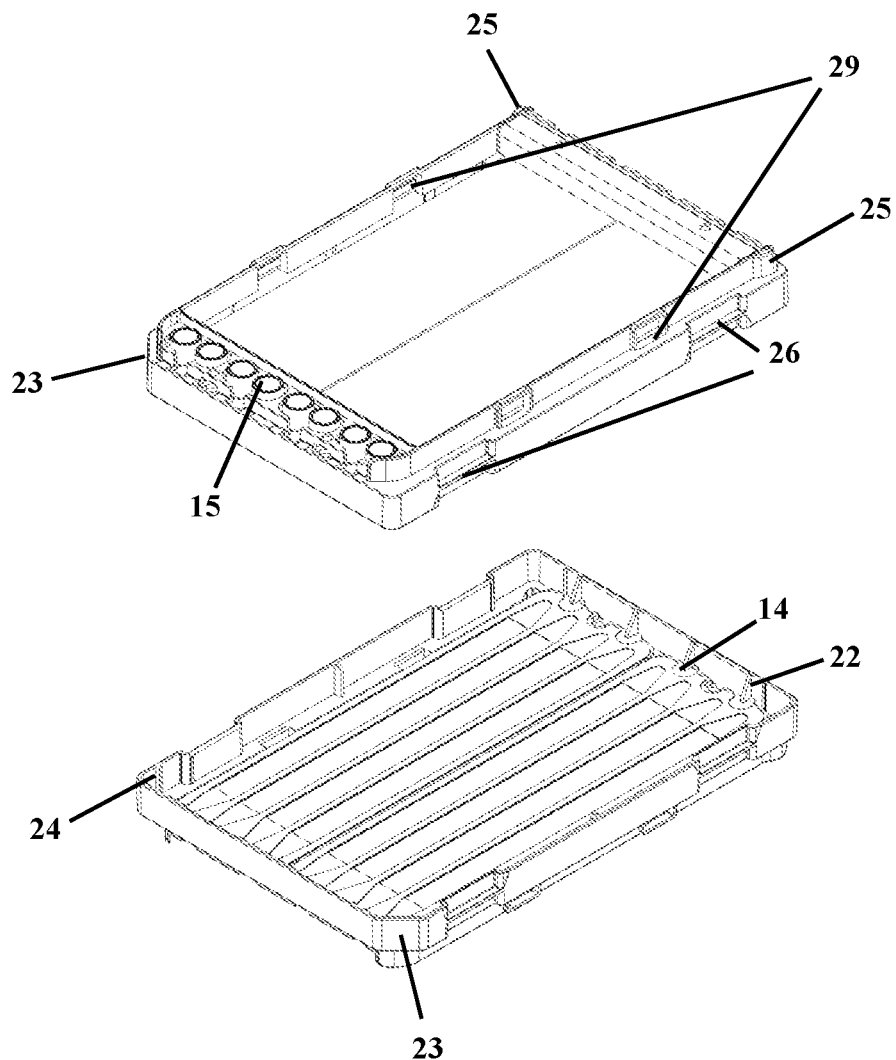
Figure 2A:
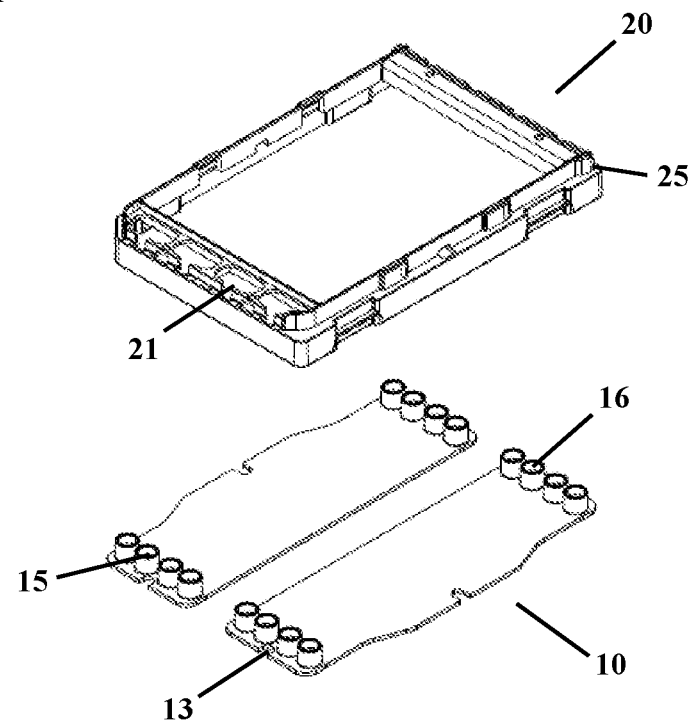
FIGS. 2A-2C provide the same views as FIG. 1 of an alternative embodiment of the multiwell plate and the frame of the analytical system described herein.
Figure 2B:
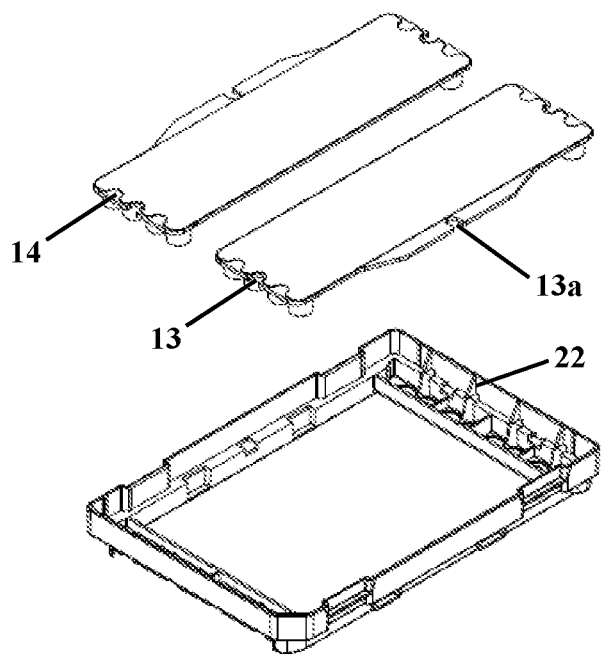
Figure 2C:
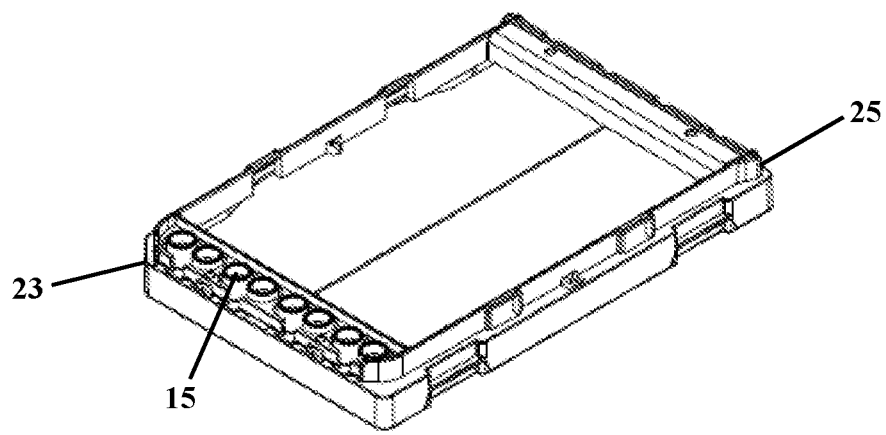
Figure 2C:
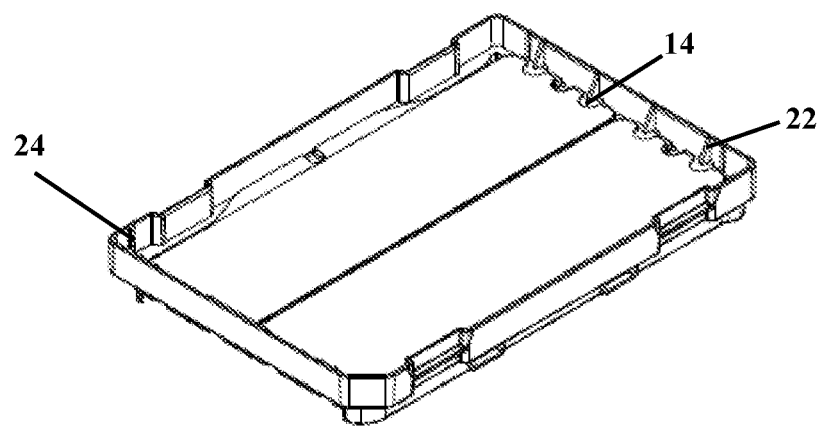

The flow-through channels (17) of this embodiment can be seen in the perspective exploded view from below shown in FIG. 1B. They contain the wells (11) of the multiwell plate (10) in an optically transparent area (12). Regarding docking/assembling functionalities, FIGS. 1A and B both show the first docking structure (13) of each multiwell plate (10), in the present embodiment being an indentation at the edge of each multiwell plate (10). The multiwell plates (10) can be held by the frame (20) in this specific embodiment by snappers (22) comprised by the frame (20) interacting with half-circle-shaped regions of reduced thickness at the rim (14) of each multiwell plate (10). As can be seen in the perspective depictions of the multiwell plate/frame assembly from above and below in FIG. 1C, the gaps (21) in the frame (20) for inlet and outlet ports (15, 16) of the multiwell plates leave a certain lateral clearance in which the latter can laterally move, thus conferring an extent of lateral flexibility of frame (20) and multiwell plate (10) relative to each other sufficient to compensate for differences in expansion of both system components. At the same time, the boundaries of the gaps (21), along with the extension of the inlet ports (15) that are surrounded by them, define the extent of lateral clearance between multiwell plate (10) and frame (20). Alternatively or additionally, the lateral clearance may be defined by the clearance between the outer limits of the multiwell plate (10) itself and the inner boundaries of the frame (20), or by the clearance of the outlet ports (16) within the frame (20). The frame (20) of FIG. 1 also shows asymmetrical structures with the purpose of "hardware coding", in this embodiment in the form of a beveled upper left corner (23) and a ridge (24) and projections (25) which together avoid incorrect orientation of the frame (20) to other frames in a stack of frames, for example, to prevent wrong stacking in loading or storage modules of an analyzer. The beveled upper left corner of the frame (23) interacts with the left corner of the baseplate (36) and thereby also avoids incorrect orientation of the frame (20) on the baseplate (30). Further visible in this depiction are gripping ridges (29) and ribs (26) for handling and holding down the frame (20) with a device such as a robotic gripper.

FIG. 2 similarly provides a perspective view of a frame (20) and an arrangement of two individual multiwell plates (10) according to another embodiment. While the structural features described above in the context of FIG. 1 are also present in the depictions of FIG. 2, the first docking structure (13) of the multiwell plates (10) comprises an additional indentation (13a) in the center of the length at one side of each multiwell plate (10), providing further stability and more accurate positioning to the multiwell plates (10) when held by a baseplate (not shown).

Figure 3A:
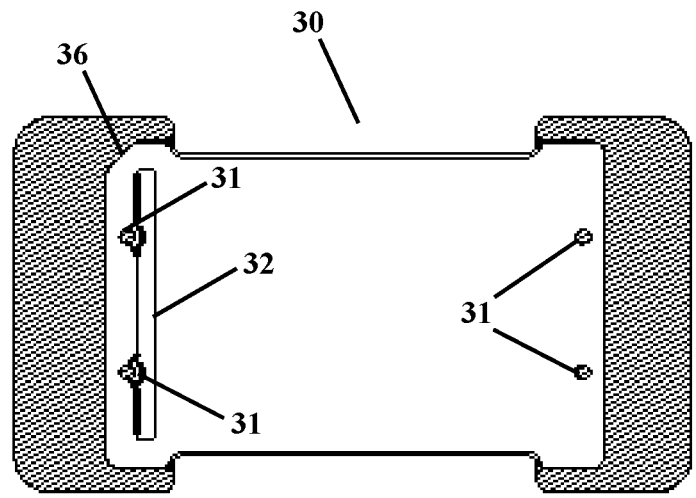
FIGS. 3A-3C show the baseplate of the analytical system described herein in a planar schematic view from above (FIG. 3A), in a perspective view with a multiwell plate/frame arrangement approaching from above (FIG. 3B), and with the multiwell plate docked to the baseplate (FIG. 3C).
Figure 3B:
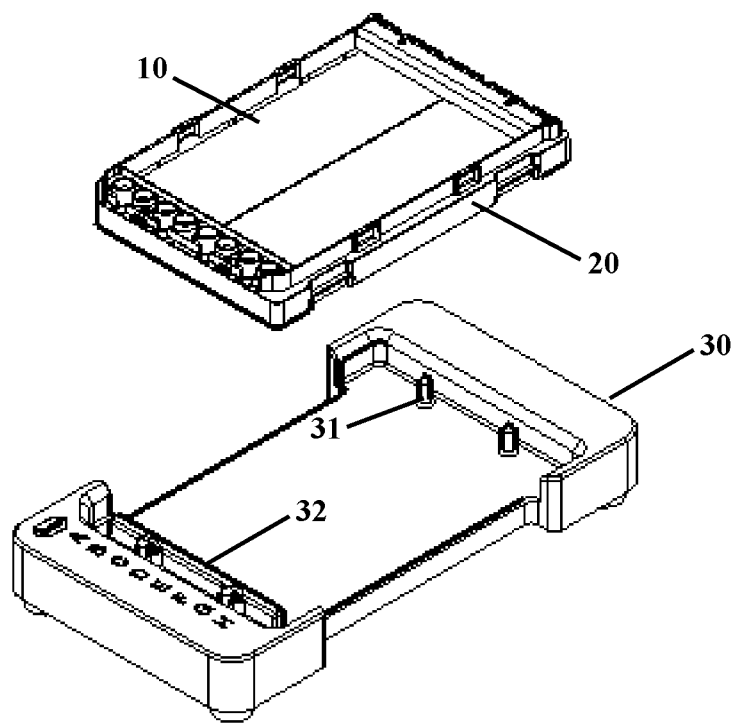
Figure 3C:
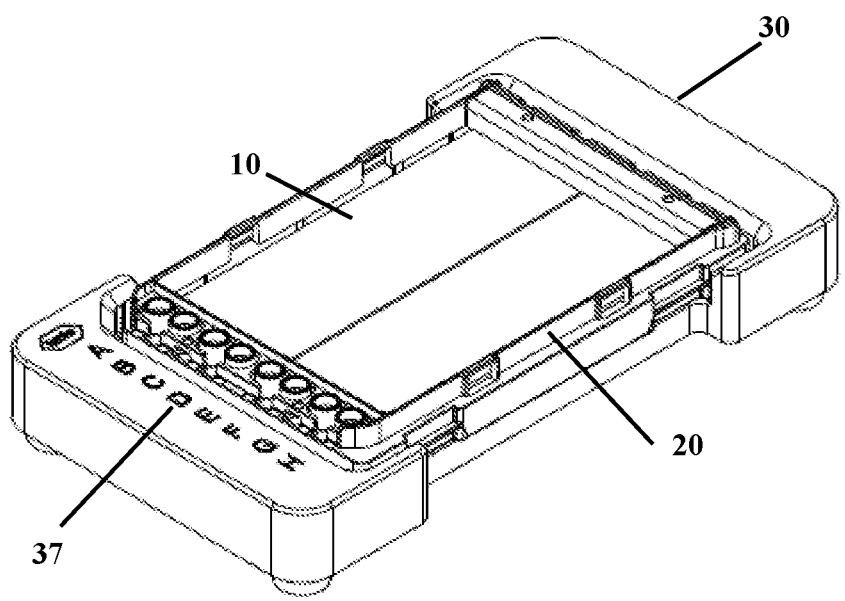

FIG. 3 shows an embodiment of the baseplate (30) described herein. A schematic top view of the baseplate (30) is provided in FIG. 3A, where the second docking structure (31) in the form of pins is visible as circles. The bar (32) is an upward protrusion from the baseplate (30) and acts as a mechanical support for the multiwell plates (10) as seen in FIG. 3B, where the inlet ports (15) left open by the frame (20) come to rest on said bar (32) when the multiwell plates (10) are docked to the baseplate (30) by means of the first (13) and the second (31) docking structures. In the fully assembled state of the analytical system described herein as shown in FIG. 3C, the purpose of the gaps (21) in the frame (20) becomes evident, as the inlet ports (15) remain accessible for pipette tips or the like, allowing for the application of a sample liquid or other fluids into the flow-through channel (17) of the multiwell plate (10). The bar (32) now supports the bottom of the inlet port (15), such that the risk of the bottom being penetrated by a pipette tip or a pipetting needle is reduced. Still in FIG. 3C, it can be seen that each of the lanes on the multiwell plates (10) is labeled with a letter (37) next to each corresponding inlet port (15). The baseplate (30) of the embodiment depicted in FIG. 3 is of a massive and non-transparent nature, as it is meant to serve as an aid for manual pipetting. In this embodiment, frame (20) and multiwell plates (10) are placed on the baseplate (30) in order to fix the inlet ports (15) such that they are kept in place while introducing a pipette tip into said inlet ports (15) manually. Consequently, the baseplate (30) of this embodiment is made of a solid material with sufficient weight for not being easily moved by accidental pushing with the pipette tip or the like. For instance, such material may be aluminum or a different kind of metal or alloy. In this embodiment, transparency of the baseplate (30) is not required. As described herein, the frame (20) and the baseplate (30) are not attached to each other via a direct fixture, thus maintaining lateral clearance between the multiwell plates (10) that are tightly laterally fixed to the baseplate (30) via the first and second docking structures, and the frame (20).

Figure 4A:
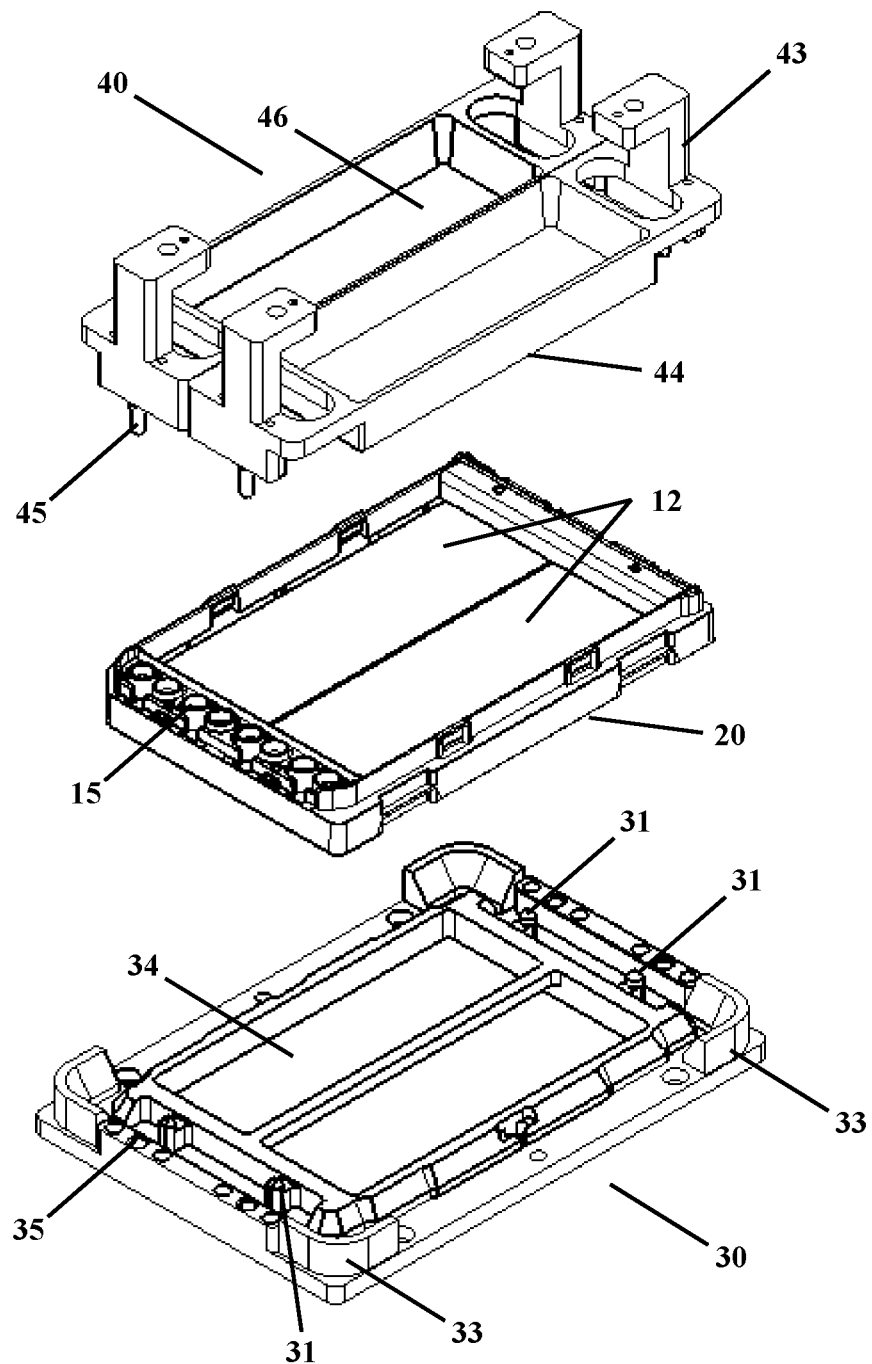
FIGS. 4A-4C depict the analytical system described herein in the context of an optical detection system. While FIG. 4A provides an exploded perspective view of the different components.

The interaction of an assembly of frame (20) and multiwell plates (10) with a baseplate (30) as a part of an optical detection system (40) is illustrated in FIG. 4. The exploded view of FIG. 4A shows—from bottom to top of the drawing—a baseplate (30), a frame (20) holding two individual multiwell plates (10) each exposing their optically transparent areas (12), and an upper part of the optical detection system (40) for pressing the multiwell plates (10) down against the baseplate (30), the latter acting as a lower part of the optical detection system (40) in order to achieve an improved vertical fixation of the multiwell plates' optically transparent areas (12) in the optical path. The chamfered corners (33) of the baseplate (30) contribute to pre-orienting the frame (20) upon approaching by guiding them, such that the second docking structure (31) in the form of pins protruding from the baseplate (30) may be smoothly led into the indentations forming the first docking structure (not shown) of the multiwell plates (10). Again, in accordance with the properties of the analytical system described herein, the baseplate (30) is docked only to the multiwell plates (10), while there is not direct fixture between baseplate (30) and frame (20). The flexible suspension of the frame (20) in relation to the baseplate (30) to which the multiwell plates (10) are docked allows for lateral clearance between frame (20) and multiwell plates (10) despite maintenance of a tight and controlled lateral fixation of the wells (11) borne by the optically transparent areas (12) of the multiwell plates (20) within the optical path. In other words, even in the case of thermal expansion of the multiwell plates (10) due to—for instance—thermal incubation during detection, or warming due to the use of high-energetic radiation in the detection system, the risk of distortion between multiwell plates (10) and frame (20) is minimized even when these components are made of different materials and thus expose different extents of aging-caused shrinkage or differential thermal expansion. Also, in processes where detection is preceded by thermocycling, such as in endpoint PCR which is typically applied in the context of digital PCR, the same analytical system described herein can be used for thermocycling in a thermocycling unit (see, for example, FIG. 5) and subsequent optical detection as currently described. Thereby, distortion phenomena can be avoided at all stages of an analytical process. For example, distortion phenomena between multiwell plate (10) or plates and frame (20) are already avoided during the intense thermal stress in a thermocycling unit, such that the multiwell plate (10) can be transferred to the detection unit without damages to its shape.

Figure 4B:
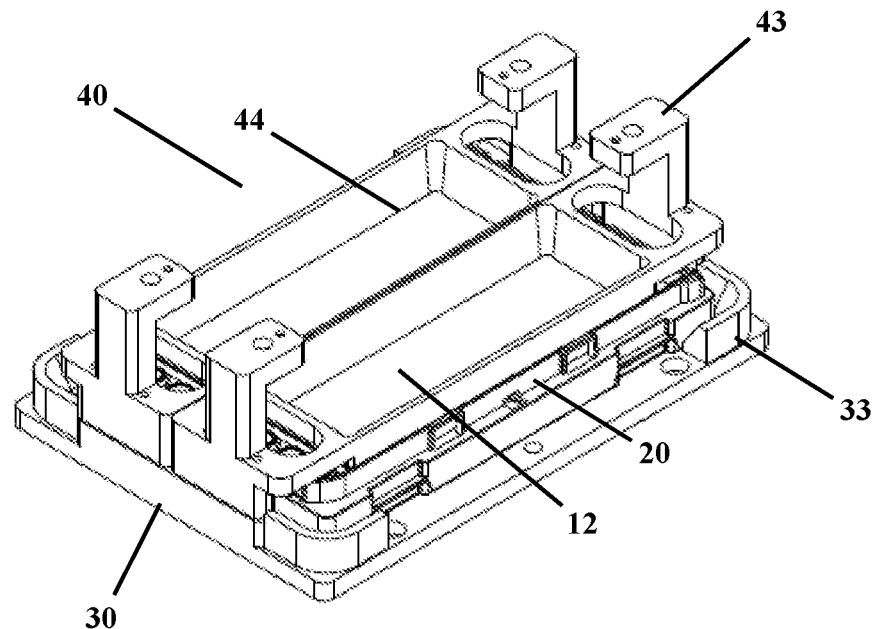
Figure 4C:
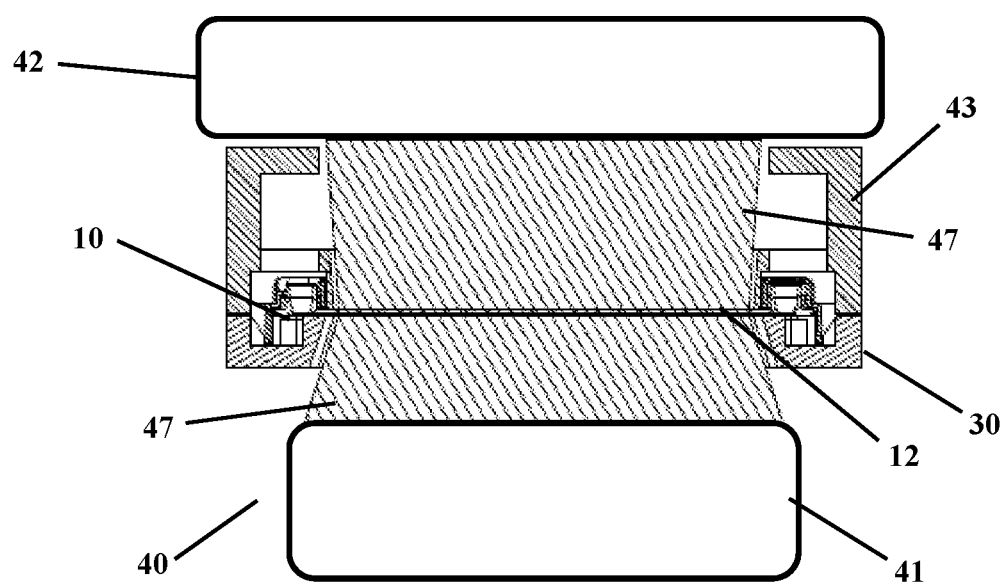

The two depicted parts of the optical detection system (40) interact with each other via another docking system including pins (45) protruding downwards from the upper part, and via corresponding recesses (35) in the baseplate (30). The upper part presses against the multiwell plates (10) only at its rims (44), such that the optical path—in this embodiment extending essentially perpendicularly to the plane corresponding to multiwell plates (10) and frame (20)—is defined by these rims (44) in conjunction with the optically transparent areas (12). Correspondingly, the optical path is left free by the gaps (34) in the body of the baseplate (30) and the gaps (46) in the upper part of the optical detection system (40). The perspective view of the fully assembled system shown in FIG. 4B illustrates how the optically transparent areas (12) are thus accessible for a light beam following the optical path. The cross-section of FIG. 4C depicts such a light beam (47) emitted by a light source (41) located underneath the baseplate (30) as it passes through the optically transparent areas (12) of the multiwell plates (10) and is received by a detector (42). In other embodiments, the positions of light source (41) and detector (42) may be swapped.

Throughout the depictions of FIG. 4, hooks (43) are visible as components of the upper part of the optical detection system (40). These hooks (43), for instance, interact with robotic grippers or other structures suitable for moving the upper part onto and away from the baseplate (30).

Figure 5:
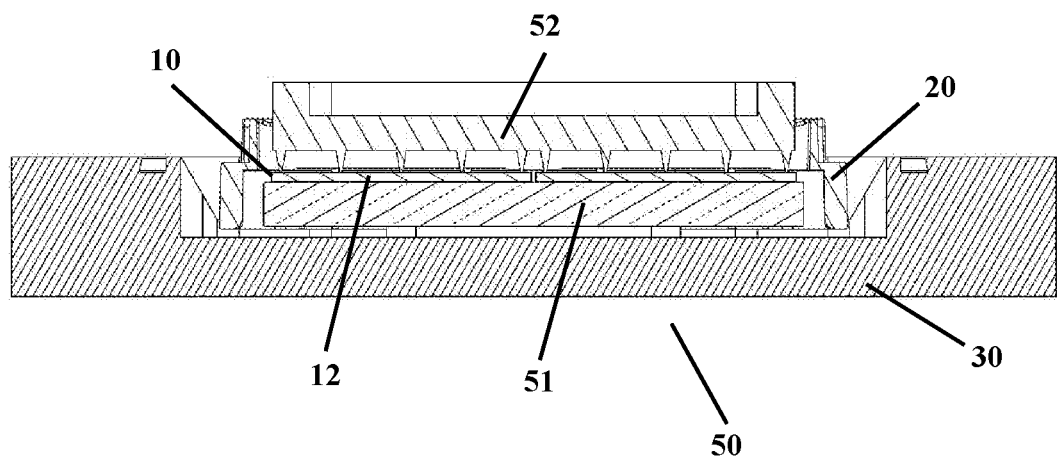
FIG. 5 is a cross-sectional view of the analytical system described herein interacting with a thermal incubation system.

FIG. 5 represents a cross-sectional side view of a thermal incubation system (50) often found in sample preparation modules, PCR analyzers (as thermocycling units) or similar devices. The baseplate (30) of this embodiment comprises an element for heating and/or cooling such as a Peltier element (51) located directly underneath the optically transparent area (12) comprising the wells of the multiwell plate (10). It can be seen that the Peltier element (51) is in thermal contact with the multiwell plate (10) but not the frame (20) due to the specific arrangement described herein, in which the multiwell plate (10) is docked to the baseplate (30) via the first and second docking structures (not shown here for the sake of clarity) while frame (20) and baseplate (30) do not directly interact with each other. By virtue of this setup, the multiwell plate (10) pressed against the Peltier element (51) or an intermediate thermotransductive element between Peltier (51) and multiwell plate (10) from above by a downholder (52), which in some embodiments may itself be heated and/or cooled for enhanced thermal homogeneity, is exposed to thermal changes that may lead to chemical or biochemical reactions such as nucleic acid amplification within the wells, while the thermal mass of the frame (20) does not significantly slow down the process by subtracting thermal energy provided by the Peltier element (51), since multiwell plate (10) and frame (20) are only in physical and thus thermal contact at few locations such as the ridges (28) shown in FIG. 1. More importantly, the lateral clearance maintained between multiwell plate (10) and frame (20) by its flexible suspension avoids warping or distortion phenomena within the multiwell plate/frame arrangement as described herein. The latter may now be transferred, for instance, to the optical detection system (40) discussed under FIG. 4, in which the flexible suspension and thus lateral clearance is further maintained and thus ensures proper and reliable positioning of the wells (11) of the multiwell plate (10) within the optical path.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. An analytical system for conducting a biological or chemical assay, the system comprising the following components:
   a) a multiwell plate comprising a rim extending along the perimeter of the multiwell plate, a plurality of wells positioned in an optically transparent area, and at least one inlet port, the multiwell plate having a first docking structure spaced apart from the optically transparent area, wherein the first docking structure comprises at least one half-circle shaped indentation disposed at the rim of the multiwell plate;
   b) a frame surrounding the rim extending along the perimeter of the multiwell plate, the frame comprising at least gap corresponding to the at least one inlet port on the multiwell plate, the at least one gap being configured to hold the multiwell plate at the rim with sufficient lateral clearance between the frame and the rim extending along the perimeter of the multiwell plate to spatially compensate for differential expansion of the frame and the multiwell plate; and
   c) a baseplate having a protruding second docking structure corresponding to the at least one half-circle shaped indentation of the first docking structure to position the multiwell plate with its plurality of wells in the optically transparent area relative to the baseplate;
   wherein there is no direct fixture between the frame and the baseplate, such that the lateral clearance between the frame and the rim extending along the perimeter of the multiwell plate is maintained when the frame is docked to the baseplate; and wherein the baseplate is functionally coupled to an optical detection system comprising a light source and detector.

2. The analytical system of claim 1, wherein the multiwell plate further comprises an outlet port connected to the inlet port by a flow-through channel.

3. The analytical system of claim 1, wherein the wrench size of each well is between 1 μm and 1 mm.

4. The analytical system of claim 1, wherein the optically transparent area comprises at least 1000 wells.

5. The analytical system of claim 1, wherein the optically transparent area comprises at least 5000 wells.

6. The analytical system of claim 1, wherein the optically transparent area comprises at least 10000 wells.

7. The analytical system of claim 1, wherein the frame holds more than one multiwell plate.

8. The analytical system of claim 1, wherein the dimensions of the frame are according to the ANSI/SLAS standards.

9. The analytical system of claim 1, wherein the first docking structure is located substantially in the center of one or more of the length and width of the edge of the multiwell plate.

10. The analytical system of claim 1, wherein the frame comprises one or more of a handle, a stacking mechanism, a hardware coding element, and an identification tag.

11. The analytical system of claim 1, wherein frame and multiwell plate are made of different materials.

* * * * *